United States Patent
Malhotra et al.

(10) Patent No.: US 11,129,836 B2
(45) Date of Patent: Sep. 28, 2021

(54) PAR-4 AGONISTS FOR THE TREATMENT OF CANCER

(71) Applicant: Cipla Limited, Mumbai (IN)

(72) Inventors: Geena Malhotra, Mumbai (IN); Kalpana Joshi, Maharashtra (IN); Jeevan Ghosalkar, Thane (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 16/420,554

(22) Filed: May 23, 2019

(65) Prior Publication Data

US 2020/0046721 A1 Feb. 13, 2020

Related U.S. Application Data

(63) Continuation of application No. 15/635,507, filed on Jun. 28, 2017, now abandoned.

(30) Foreign Application Priority Data

Jun. 28, 2016 (IN) .............................. 201621022084

(51) Int. Cl.
*A61K 31/545* (2006.01)
*A61K 38/00* (2006.01)
*A61K 39/395* (2006.01)
*A61K 31/546* (2006.01)
*A61K 45/06* (2006.01)
*A61K 39/00* (2006.01)

(52) U.S. Cl.
CPC ............ *A61K 31/546* (2013.01); *A61K 45/06* (2013.01); *A61K 39/00* (2013.01); *A61K 39/39558* (2013.01)

(58) Field of Classification Search
CPC ...................................................... A61K 31/431
USPC ....................................................... 514/207
See application file for complete search history.

(56) References Cited

U.S. PATENT DOCUMENTS

| 7,183,257 B2 | 2/2007 | Xiao |
| 7,482,334 B2 | 1/2009 | Frincke et al. |
| 2014/0120083 A1* | 5/2014 | Stern ...................... A61K 45/06 424/133.1 |

FOREIGN PATENT DOCUMENTS

WO 2012100248 7/2012

OTHER PUBLICATIONS

Colizza et al. "Short-term prophylaxis with cefuroxime in colorectal surgery for cancer," J. Surgical Oncology, 1987, vol. 35, pp. 266-268. (Year: 1987).*
Hebbar et al. Mechanism of Apoptosis by the tumor suppressor Par-4, J. Cell. Physiol. 227:3715-3721, 2012. (Year: 2012).
Armstrong "Life threatening infections in cancer patients" Wiley on line library, 1973, https://onlinelibrary.wiley.com/doi/pdf/10.3322/canjclin.23.3.138. (Year: 1973).

* cited by examiner

*Primary Examiner* — Shengjun Wang
(74) *Attorney, Agent, or Firm* — Meunier Carlin & Curfman LLC

(57) ABSTRACT

Disclosed herein are methods of treating cancers by administration of a PAR-4 agonist.

8 Claims, 1 Drawing Sheet

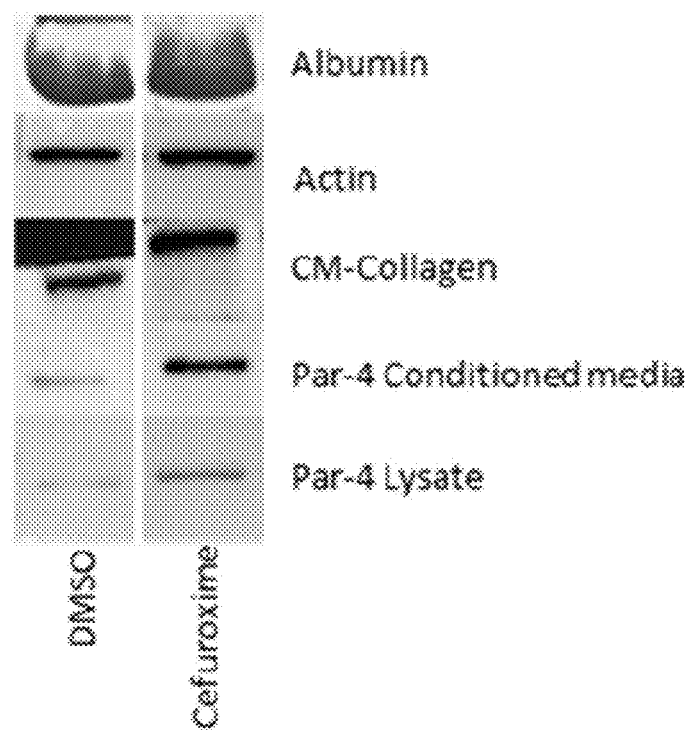

PAR-4 AGONISTS FOR THE TREATMENT OF CANCER

CROSS REFERENCE TO RELATED APPLICATION

This application is a continuation of U.S. application Ser. No. 15/635,507, filed Jun. 28, 2017, which claims the benefit of Indian Application 201621022084, filed on Jun. 28, 2016, the contents of which are hereby incorporated in its entirety.

FIELD OF THE INVENTION

The present invention relates to the treatment of cancer, specifically to a method of treating cancer by administering a PAR-4 agonist to a patient in need thereof.

BACKGROUND

Cancer is a major public health problem in the United States and many other parts of the world. It is currently the second leading cause of death in the United States, and is expected to surpass heart diseases as the leading cause of death in the next few years. It remains a major cause of mortality in the world. Despite the improvements that have been made in therapies and in understanding the molecular basis of cancer, mortality is still high. The current treatment regimens for cancer have shown limited survival benefits when used for most advanced stage cancers.

The research and efforts being invested for cancer treatment has changed over the past few decades. The age when surgery and radiotherapy were the only effective way to fight tumor growth has ended. A complex scenario where the molecular features of tumors seem to be the cornerstone of any therapy is now emerging with new targets or receptors being discovered in vivo. Continued research has expanded knowledge of how cancer develops and how to target medicines for specific cancer types, which has resulted in more effective therapies for patients. However these therapies show a lack of efficacy in terms of long-term outcome because of their failure to target cancer cells and lead to toxicity due to non-specific effects on normal cells. To overcome these side effects, researchers have tried to understand the root cause and have explored more about the gene changes in cells that cause cancer, they have been able to develop drugs that target these changes. Targeted therapy drugs does not work in the same way as the standard chemotherapy drugs. They are often able to attack cancer cells while doing less damage to normal cells by targeting the programming of cancer cells that sets them apart from normal, healthy cells. These drugs tend to have different (and often less severe) side effects than standard chemotherapy drugs. Examples of the targeted therapies include sorafenib, sunitinib, bevacizumab, telomerase etc.

Research on apoptosis has increased substantially since the early 1990s. Apoptosis (programmed cell death)-inducing drugs change proteins within the cancer cells and cause the cells to die.

Apoptosis can be initiated through one of two pathways. In the intrinsic pathway the cell kills itself because it senses cell stress, while in the extrinsic pathway the cell kills itself because of signals from other cells. Both pathways induce cell death by activating caspases, which are proteases, or enzymes that degrade proteins. The two pathways both activate initiator caspases, which then activate executioner caspases, which then cause cell apoptosis by degrading proteins indiscriminately.

Induction of apoptosis in malignant cells therefore becomes a major goal of cancer therapy in general and of certain cancer gene therapy strategies in particular. Numerous apoptosis-regulating genes have been evaluated for this purpose for example p53 gene, p16, p21, p2'7, E2F genes, FHIT, PTEN, E1A and CASPASE genes.

The prostate apoptosis response-4 (PAR-4) gene was first identified by the differential hybridization technique as an immediate early apoptotic gene upregulated in response to elevated intracellular Ca2+ concentration [Ca2+] in the androgen-independent rat prostate cancer cells AT-3 treated with ionomycin (Sells S F, et al; *Cell Growth Differ.* 1994 April; 5(4):457-66).

Studies conducted in cell culture models show that overexpression of PAR-4 is sufficient to directly induce apoptosis in many cancer cell types. The ability of PAR-4 to directly cause apoptosis is associated with its nuclear translocation. Moreover, the apoptotic action of PAR-4 can overcome cell protective mechanisms, such as the presence of Bcl-xL, Bcl-2, or absence of wild-type p53 or PTEN function. Interestingly, PAR-4 is incapable of directly inducing apoptosis in normal or immortalized normal cells.

The "apoptosis-sensitizing" function of PAR-4 in some of the cancer cells is attributed to its accumulation in the cytoplasm and inability to translocate into the nucleus, due to phosphorylation by Akt1 which renders PAR-4 subject to sequestration in the cytoplasm by complexing it with chaperone proteins such as 14-3-3 (Goswami et al., *Mol Cell.* 2005 Oct. 7; 200:33-44); however, treatment with the other apoptotic signals translocates PAR-4 into the nucleus to produce apoptosis.

Thus there is a need for improved methods for treating cancer. There remains a need for selective PAR-4 agonists. There remains a need for identifying selective PAR-4 agonists useful in the treatment of cancer.

SUMMARY

According to an aspect of the present invention, there is provided a method for enhancing or promoting PAR-4 expression by administering a PAR-4 agonist. In some instances the PAR-4 agonist is a cephalosporin antibiotic, for instance a second generation cephalosporin antibiotic such as cefuroxime, salts and prodrugs thereof.

According to an aspect of the present invention, there is provided a method of treating cancer comprising administering by administering a PAR-4 agonist. In some instances the PAR-4 agonist is a cephalosporin antibiotic, for instance a second generation cephalosporin antibiotic such as cefuroxime, salts and prodrugs thereof.

According to an aspect of the present invention, there is provided a method of treating cancer comprising administering by administering a PAR-4 agonist as part of a cancer treatment regimen. In some instances the PAR-4 agonist is a cephalosporin antibiotic, for instance a second generation cephalosporin antibiotic such as cefuroxime, salts and prodrugs thereof. The cancer treatment regimen can include administration of one or more additional PAR-4 agonists, one or more additional chemotherapeutic agents, exposure to ionizing radiation, and/or surgical interventions.

According to an aspect of the present invention, there is provided a method of treating cancer comprising administering cefuroxime, or a salt or prodrug thereof, in combination with one or more additional chemotherapeutic agents, in which the additional chemotherapeutic agents are administered with cefuroxime either simultaneously, sequentially, or separately.

The details of one or more embodiments are set forth in the descriptions below. Other features, objects, and advantages will be apparent from the description and from the claims.

BRIEF DESCRIPTION OF THE FIGURES

FIG. 1 depicts a Western blot analysis demonstrating that cefuroxime causes increased PAR-4 secretion in mouse embryonic fibroblast cells.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The compounds disclosed herein may be formulated as a pharmaceutically acceptable salt. Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, ptoluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

The cephalosporin antibiotics disclosed herein may be formulated as pharmaceutically acceptable prodrugs. Typically formed as ester with the 4-carboxylic acid group, prodrugs can substantially increase the bioavailability of the compounds, permitting more effective oral therapy. Such esters include $C_1$-$C_{10}$ alkyl esters, which may or may not be substituted. A preferred substituent is carbonyl-oxy and alkyloxy-carbonyloxy. Exemplary esters include pivaloyloxy-methyl ester, 1-(isopropyloxy-carbonyloxy)ethyl ester, and 1-(acetyloxy)ethyl ester. Unchecked cell growth is a characteristic of all cancers. Suppression of growth inhibitory or apoptotic functions by growth stimulatory or cell survival proteins is seen in human cancer. The coupling between cell division and cell death is thought to act as a barrier that cells must overcome for cancer initiation and progression. This may be the underlying reason why cancer cells often over express anti-apoptotic proteins such as Bcl-2, Bcl-xL and survivin, along with inactivation of pro-apoptotic tumor-suppressor proteins p53, p19arf, PAR-4 and PTEN that control apoptosis pathways, generating severe defects in the balance between cell division and pro-grammed cell death in cancer settings. Thus the mentioned abnormalities that generate defects in apoptotic pathways allow cancer cells to survive.

The inventors of the present invention have surprisingly found that cefuroxime is a potent secretor or agonist of prostate apoptosis response-4 (PAR-4). As such, cefuroxime can be used to treat PAR-4 associated cancers, either alone or in combination with other cancer therapy regimens.

The terms "induces, "secretor" or "agonist" are used interchangeably throughout the specification, all the terms indicate that the drug increases the expression of PAR-4.

The term "combination" as used herein, defines either a fixed combination in one unit dosage form, a non-fixed combination or a kit of parts for the combined administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease.

PAR-4 is a pro-apoptotic, tumor suppressor protein. It is found to be deregulated in several cancers. Several studies have documented the association of low level of PAR-4 with poor prognosis in cancers of prostate, endometrial, renal, pancreas, and breast. Endoplasmic reticulum-stress and higher levels of protein kinase A in tumor cells confer the coveted feature of cancer selective response to extracellular and intracellular PAR-4, respectively. Recent studies have shown that systemic PAR-4 confers resistance to tumor growth in mice.

PAR-4 is a leucine zipper domain protein identified in cells undergoing apoptosis in response to exogenous insults. PAR-4 is expressed ubiquitously among the various tissue types, and resides in both the cytoplasm and the nucleus. Although endogenous PAR-4 is largely inactivated, and does not produce extensive apoptosis by itself, it is essential for the apoptotic function of diverse cytotoxic agents. Interestingly, PAR-4 over-expression is sufficient to induce apoptosis in most cancer cells, but not in normal or immortalized cells.

PAR-4 has been shown to activate apoptosis through intrinsic and extrinsic pathways. Upregulation or induction of PAR-4 by apoptotic stimuli such as tumor necrosis factor alpha (TNFα), TRAIL and Fas induce cell death in cancer cells. Other studies showed that overexpression of PAR-4 enhances the activity of anticancer drugs such as 5-fluorouracil and induces radio-sensitivity. While the intracellular role of PAR-4 is established and the mechanisms well studied, recent studies have demonstrated that secretory or extracellular PAR-4 induces apoptosis in cancer cells (Shastri et al., 2015).

Previous studies suggest that the role of PAR-4 in apoptosis is cancer cell selective in that (i) overexpression of PAR-4 triggers apoptosis in various cancer cell lines but not in normal and primary cells, (ii) depletion of PAR-4 by RNA interference (RNAi) confers resistance in cancer cells, but not in primary fibroblasts, to various apoptotic agents, and (iii) PAR-4 displays proapoptotic functions in cells transformed with oncogene Ras but not in normal cells. Recently, PAR-4 was shown to be secreted by mammalian cells and, through interaction with the cell surface receptor GRP78, to induce cancer cell apoptosis in a specific manner.

PAR-4 is found to be down regulated in several cancers like prostate, endometrial, renal, pancreas, and breast. Also because the baseline levels of PAR-4 secreted by normal cells are generally inadequate to cause massive apoptosis in cancer cell, secretogogues that bolster the release of PAR-4 constitute an important therapeutic advance. For example, Nutlin-3a, originally developed as an MDM2 inhibitor, stimulated PAR-4 secretion at micromolar levels in mouse embryonic fibroblast (MEF) cells.

The inventors of the present invention have surprisingly found through various studies that cefuroxime, being an antibiotic, has been found to increase the secretion of PAR-4 protein.

Cefuroxime has a chemical nomenclature of (6R, 7R)-3-{[(aminocarbonyl) oxy] methyl}-7-{[(2Z)-2-(2-furyl)-2-(methoxyimino) acetyl]amino}-8-oxo-5-thia-1-azabicyclo [4.2.0]oct-2-ene-2-carboxylic acid and is chemically represented as—

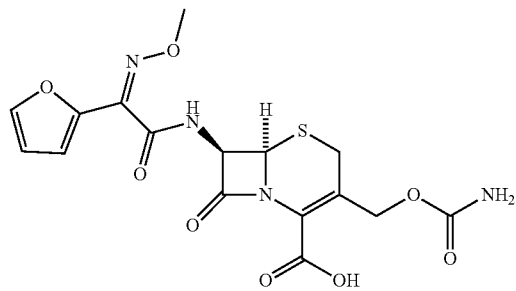 [SMILES: CO/N=C(\C(=O)N[C@@H]1C(=O)N2C(C(=O)O)=C(COC(N)=O)CS[C@H]12)c1ccco1]

The term "cefuroxime" as per present invention is used in broad sense to include not only "cefuroxime" per se but also its pharmaceutically acceptable derivatives thereof. Suitable pharmaceutically acceptable derivatives include pharmaceutically acceptable salts like sodium, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc. Preferably, the cefuroxime used to treat cancer is cefuroxime axetil (i.e., cefuroxime 1-(acetyloxy)ethyl ester).

The types of cancers which may be treated using PAR-4 agonists include: acute lymphoblastic leukemia (ALL), acute myeloid leukemia (AML), cancer in adrenocortical carcinoma, adrenal cortex cancer, AIDS-related cancers, Kaposi sarcoma, AIDS-related lymphoma, primary CNS lymphoma, anal cancer, appendix cancer, carcinoid tumors, astrocytomas, atypical teratoid/rhabdoid tumor, basal cell carcinoma, skin cancer (nonmelanoma), bile duct cancer, extrahepatic bladder cancer, bladder cancer, bone cancer (includes Ewing sarcoma and osteosarcoma and malignant fibrous histiocytoma), brain tumors, breast cancer, bronchial tumors, Burkitt lymphoma (non-Hodgkin), carcinoid tumor, cardiac (heart) tumors, atypical teratoid/rhabdoid tumor, embryonal tumors, germ cell tumors, lymphoma, primary—cervical cancer, cholangiocarcinoma, chordoma, chronic lymphocytic leukemia (CLL), chronic myelogenous leukemia (CML), chronic myeloproliferative neoplasms, colorectal cancer, colorectal cancer, craniopharyngioma, cutaneous T-cell lymphoma, ductal carcinoma in situ (DCIS), embryonal tumors, central nervous system, endometrial cancer, ependymoma, esophageal, esthesioneuroblastoma, ewing sarcoma, extracranial germ cell tumor, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastric (stomach) cancer, gastrointestinal carcinoid tumor, gastrointestinal stromal tumors (GIST), gastrointestinal stromal tumors (GIST), germ cell tumors, central nervous system, extracranial, extragonadal, ovarian testicular, gestational trophoblastic disease, gliomas, hairy cell leukemia, head and neck cancer, heart tumors, hepatocellular (liver) cancer, histiocytosis, Langerhans Cell, Hodgkin's lymphoma, hypopharyngeal cancer, intraocular melanoma, islet cell tumors, pancreatic neuroendocrine tumors, Kaposi sarcoma, kidney—langerhans cell histiocytosis, laryngeal cancer, laryngeal cancer and papillomatosis, leukemia, lip and oral cavity cancer, liver cancer (primary), lung cancer, lung cancer, lymphoma—macroglobulinemia, Waldenström-Non-Hodgkin lymphoma, male breast cancer, malignant fibrous histiocytoma of bone and osteosarcoma, melanoma, intraocular (eye), Merkel cell carcinoma, mesothelioma, malignant, mesothelioma, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (CIVIL), myeloid leukemia, acute (AML), nasal cavity and paranasal sinus cancer, nasopharyngeal cancer, nasopharyngeal cancer, neuroblastoma, non-hodgkin lymphoma, non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), papillomatosis, paraganglioma, paraganglioma, paranasal sinus and nasal cavity cancer, parathyroid cancer, penile cancer, pharyngeal cancer, pheochromocytoma, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, retinoblastoma, rhabdomyosarcoma, salivary gland cancer, salivary gland tumors, Ewing sarcoma, Kaposi sarcoma, osteosarcoma, rhabdomyosarcoma, uterine sarcoma, vascular tumors, Sézary syndrome, skin cancer, small cell lung cancer, small intestine cancer, soft tissue sarcoma, squamous cell carcinoma, squamous neck cancer with occult primary, metastatic, stomach (gastric) cancer, stomach (gastric) cancer, T-cell lymphoma, cutaneous, testicular cancer, throat cancer, thymoma and thymic carcinoma, thyroid cancer, ureter and renal pelvis, transitional cell cancer, urethral cancer, uterine cancer, endometrial and uterine sarcoma, vaginal cancer, vaginal cancer, vascular tumors, vulvar cancer, Waldenström Macroglobulinemia, Wilms Tumor.

In certain preferred embodiments, cefuroxime can be used to treat prostate cancer, breast cancer, lung cancer, or skin cancer/melanoma. In particular, cefuroxime can be used to treat superficial spreading melanoma, nodular melanoma, lentigno maligna melanoma, and desmoplastic melanoma. In some embodiments, the patient to be treated does not have renal cancer.

Depending on the pathological stage, patient's age and other physiological parameters, size of the tumor, and the extent of invasion, the pharmaceutical composition comprising cefuroxime may require specific dosage amounts and specific frequency of administrations. Preferably, cefuroxime may be administered at least once or multiple times a day in the dosage range from about 1 mg/kg/per day to about 100 mg/kg/per day. In some embodiments, cefuroxime can be administered once, twice, three times, or greater than three times a day, for a period of 1 week, 2 weeks, 4 weeks, 8 weeks, 12 weeks, 16 weeks, 20 weeks, 24 weeks, 28 weeks, 32 weeks, 42 weeks or 52 weeks. In some instances, cefuroxime can be administered intermittently, for instance for a period of 1-10 days, followed by a period in which no cefuroxime is administered (e.g., 1-10 days), followed by another period e.g., 1-10 days, in which cefuroxime is administered. The on/off dosing schedule can be repeated as many times as necessary.

In certain embodiments, cefuroxime can be administered in combination with one or more chemotherapeutic agents. Exemplary agents include Abiraterone, Methotrexate, Abraxane (Paclitaxel Albumin-stabilized Nanoparticle Formulation, Brentuximab Vedotin, Ado-Trastuzumab, Emtansine, Adriamycin, Afatinib, Everolimus, Akynzeo (Netupitant and Palonosetron Hydrochloride), Imiquimod, Aldesleukin, Alectinib, Alemtuzumab, Melphalan, Pemetrexed, Palonosetron, Chlorambucil, Aminolevulinic Acid, Anastrozole, Aprepitant, Pamidronate, Anastrozole, Exemestane, Nelarabine, Arsenic Trioxide, Ofatumumab, Asparaginase *Erwinia chrysanthemi*, Atezolizumab, Bevacizumab, Axitinib, Azacitidine, BEACOPP, Carmustine, Belinostat, Bendamustine, BEP, Bevacizumab, Bexarotene, Tositumomab, Bicalutamide, Carmustine, Bleomycin, Blinatumomab, Bortezomib, Bosutinib, Brentuximab Vedotin, Busulfan, Cabazitaxel, Cabozantinib-Alemtuzumab), Irinotecan, Capecitabine, CAPDX, Fluorouracil, Carboplatin, carboplatin-taxol, Carfilzomib, Carmustine, Bicalutamide, Lomustine, CEM, Ceritinib, Daunorubicin, Cervarix (Recombinant HPV Bivalent Vaccine), Cetuximab, Chlorambucil, CHOP, Cisplatin, Clofarabine, CMF, Cobimetinib, Cabozantinib, COPDAC, COPP, COPP-ABV, Dactinomycin, Cobimetinib, Crizotinib, CVP, Ifosfamide, Ramucirumab, Cytarabine, Cyclophosphamide, Dabrafenib, Dacarbazine, Decitabine, Dactinomycin, Daratumumab, Dasatinib, Daunorubicin, efibrotide Sodium, Defibrotide, Degarelix, Denileukin Diftitox, Denosumab, DepoCyt (Cytarabine Liposome), Dexamethasone, Dexrazoxane Dinutuximab, Docetaxel, Doxorubicin, Dacarbazine, Rasburicase, Epirubicin, Elotuzumab, Oxaliplatin, Eltrombopag Olamine, Aprepitant, Empliciti (Elotuzumab), Enzalutamide, Epirubicin, EPOCH, Cetuximab, Eribulin, Vismodegib, Erlotinib, Erwinaze (Asparaginase, *Erwinia chrysanthemi*), Etopophos (Etoposide Phosphate), Etoposide, Etoposide Phosphate, Everolimus, Evista (Raloxifene Hydrochloride), Evomela (Melphalan Hydrochloride), Exemestane, 5-FU, Fareston (Toremifene), Farydak (Panobinostat), Faslodex (Fulvestrant), FEC, Letrozole, Filgrastim, Fludarabine, Flutamide, Methotrexate, Folfiri, Folfiri-Bevacizumab, Folfiri-Cetuximab, Folfirinox, Folfox, Pralatrexate, FU-LV, Fulvestrant, Gardasil (Recombinant HPV Quadrivalent Vaccine), Obinutuzumab, Gefitinib, Gemcitabine, Gemtuzumab Ozogamicin, Afatinib, Imatinib, Carmustine, Glucarpidase, Goserelin Acetate, Eribulin, Trastuzumab, Topotecan, HydroxyureaPalbociclib), Ibritumomab Tiuxetan, Ibrutinib, ICE, Ponatinib, Idarubicin, Idelali sib, Ifex (Ifosfamide), Ifosfamide, IL-2 (Aldesleukin), Imatinib Ibrutinib, Imiquimod, Imlygic, Talimogene Laherparepvec, Axitinib, Interferon Alfa-2b, Recombinant, Interleukin-2, Aldesleukin), Intron A (Recombinant Interferon Alfa-2b), Tositumomab, Ipilimumab, Gefitinib, Irinotecan, Romidepsin, Ixabepilone, Ixazomib, Ruxolitinib, Cabazitaxel, Ado-Trastuzumab Emtansine), Raloxifene, Palifermin, Pembrolizumab, Carfilzomib, Lanreotide, Lapatinib, Lenalidomide Lenvatinib, Letrozole, Leucovorin, Leukeran, Chlorambucil), Leuprolide, Olaparib, Vincristine, Procarbazine, Mechlorethamine, Megestrol, Trametinib, Melphalan, Mercaptopurine, Mesna, Temozolomide, Methotrexate, Mitomycin C, Mitoxantrone, MOPP, Plerixafor, Mechlorethamine, Busulfan, Azacitidine, Gemtuzumab Ozogamicin, Vinorelbine, Necitumumab, Nelarabine, Neosar (Cyclophosphamide), Netupitant and Palonosetron Hydrochloride, Neupogen (Filgrastim), Nexavar (Sorafenib Tosylate), Nilotinib, Ninlaro (Ixazomib Citrate), Nivolumab, Nolvadex (Tamoxifen Citrate), Nplate (Romiplostim), Obinutuzumab, Odomzo (Sonidegib), OEPA, Ofatumumab, Olaparib, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia, Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan, ituximab), Rituximab, Rolapitant Hydrochloride, Romidepsin, Romiplostim, Rubidomycin, Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), Tabloid (Thioguanine), TAC, Tafinlar (Dabrafenib), Tagrisso (Osimertinib), Talimogene Laherparepvec, Tamoxifen Citrate, Tarabine PFS (Cytarabine), Tarceva (Erlotinib Hydrochloride), Targretin, Bexarotene), Tasigna (Nilotinib), Taxol (Paclitaxel), Taxotere (Docetaxel), Tecentriq, Atezolizumab), Temodar (Temozolomide), Temozolomide, Temsirolimus, Thalidomide, Thalomid (Thalidomide), Thioguanine, Thiotepa, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), Trabectedin, Trametinib, Trastuzumab, Treanda, Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, Vandetanib, VAMP, Varubi (Rolapitant Hydrochloride), Vectibix (Panitumumab), Velban (Vinblastine Sulfate), Velcade (Bortezomib), Velsar (Vinblastine Sulfate), Vemurafenib, Venclexta (Venetoclax), Venetoclax, Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Vistogard (Uridine Triacetate), Voraxaze, Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate). Preferred additional agents include tamoxifen, bendamustine, cladribine, or a combination thereof Cefuroxime can be administered with one or more chemotherapeutic agents either simultaneously, sequentially, or separately. In certain cases, cefuroxime can be administered for a period of at least 1 week, at least 2 weeks, at least 4 week, at least 6 weeks, at least 8 week, or at least 10 weeks, prior to commencing treatment with additional chemotherapeutic agents. In some instances, cefuroxime and the other agent can be administered intermittently, for instance a period of cefuroxime administration, followed by a period in which the other agent to administered, followed by another period of cefuroxime administration. The cycle can be repeated as many times as necessary.

In certain cases, the combination of cefuroxime and additional agent will exhibit a greater than additive effect (i.e., a synergistic effect). In other instance, the use of cefuroxime permits a reduced amount of the other agent to be administered, without a corresponding decrease in therapeutic efficiency.

In some instances, cefuroxime can be used in combination with ionizing radiation and/or surgical interventions for the treatment of cancer. Cefuroxime can be administered before, during, or after treatment with ionizing radiation or surgical intervention. In certain cases, cefuroxime can be administered for a period of at least 1 week, at least 2 weeks, at least 4 week, at least 6 weeks, at least 8 week, or at least 10 weeks, prior to commencing treatment with ionizing radiation or surgery. Exemplary forms of radiation include x-rays, gamma rays, electron beams and proton beams. It has been found that administration of cefuroxime permits a reduction in the total exposure of the patient to ionizing radiation, without a corresponding reduction in therapeutic efficiency. In certain instances, cefuroxime can be administered both prior and subsequent to ionizing radiation and/or surgical interventions.

The use of cefuroxime may preferably be associated with one or more of the above referenced anti-cancer drugs as a combination therapy (either of the same functional class or other) depending on various factors like drug-drug compatibility, patient compliance and other such factors wherein the said combination therapy may be administered either simultaneously, sequentially, or separately for the treatment of cancer.

It may be well appreciated by a person skilled in the art that the pharmaceutical composition comprising cefuroxime in combination with one or more anti-cancer drugs may require specific dosage amounts and specific frequency of administrations specifically considering their individual established doses, the dosing frequency, patient adherence and the regimen adopted. As described herein, considering that there are various parameters to govern the dosage and administration of the combination composition as per the present invention, it would be well acknowledged by a person skilled in the art to exercise caution with respect to the dosage, specifically, for special populations associated with other disorders.

Preferably, cefuroxime may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention. The pharmaceutical composition may further include one or more additional therapeutic agents as described above. In other instances, cefuroxime may be provided as a component in a kit that also contains one or more additional therapeutic agents, or instructions for administering cefuroxime to a patient in need thereof.

The inventors of the present invention have also found that the solubility properties of cefuroxime may be improved by nanosizing thus leading to better bioavailability and dose reduction of the drug.

In one embodiment, cefuroxime may be present in the form of nanoparticles which have an average particle size of less than 2000 nm.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Cefuroxime Induced PAR-4 Secretion

A. Assay Protocol to Analyse Non-Cytotoxic Concentration

Mouse embryonic fibroblast cells were plated in 96-well cell culture plates ($2\times10^4$ cells/well) and were treated with drug/s at various concentrations. Treated cells were maintained at 37° C. in 5% $CO_2$ for 96 hrs. After the incubation anti-proliferative activity of test compounds was measured using ProMega Cell Titer aqueous one solution cell proliferation assay kit, viz. CellTiter 96® AQueous One Solution Reagent. Cells were incubated for 1-4 hours at 37° C., 5% $CO_2$ incubator and absorbance was measured at 490 nM using a plate reader. $IC_{50}$ values were determined by plotting compound concentration versus cell viability.

B. Assay Protocol to Analyze PAR-4 Secretion

Material: DMEM media, FBS, Mouse embryonic fibroblast cells, PAR-4 antibody, Antirabbit IgG-HRP, Collagen A1 antibody, B-actin antibody, Antimouse IgG HRP Day 1: Cell Seeding Six well plate seeded (2 ml per well) with Mouse embryonic fibroblast cells in DMEM+10% FBS. The plate was incubated for 16-18 hrs, 37° C. 5% $CO_2$.

Day 2: Drug Addition

Drugs to be tested are diluted with suitable solvent to obtain 25 mM concentration. Media from cells is discarded and replaced with DMEM media with 0.1% FBS. Compound added to the cells at final concentration of 25 µM.

Day 3: Sample Preparation

Conditioned media (CM-supernatant) is collected from each well and centrifuged at 1000 rpm/5 mins to remove cell debris. After centrifugation the media was poured in concentration filters (Amicon ultracentrifuge tube with cutoff 10 Kda) and again centrifuged at 4500 rpm/15 mins at 4° C. The media was concentrated to 100 µl and then mixed with 50 µl of loading dye. The mixture was maintained in a 100° C. dry bath/water bath for 10 mins. SDS-PAGE and a western blot was performed of the samples using broad range molecular weight marker.

C. In Vitro Cytotoxicity on Cancer Cells

Various cancer cells lines were plated in 96-well cell culture plates ($2\times10^4$ cells/well) and were treated with drug/s at various concentrations. Treated cells were maintained at 37° C. in 5% $CO_2$ for 96 hrs. After the incubation the antiproliferative activity of test compounds was measured using ProMega Cell Titer aqueous one solution cell proliferation assay kit, viz. CellTiter 96® Aqueous One Solution Reagent. Cells were incubated for 1-4 hours at 37° C., 5% $CO_2$ incubator and absorbance was measured at 490 nM using a plate reader. $IC_{50}$ values were determined by plotting compound concentration versus cell viability.

Results

A. Non-Cytotoxic Concentration Determination:

Cefuroxime does not show toxicity in Mouse Embryonic fibroblast cells up to 48 hours at the highest concentration of 125 µM.

B. Par-4 Secretion:

1. Cefuroxime exhibited 4-5-fold increase in the secretion of PAR-4 in the conditioned media from the mouse embryonic fibroblast cells when compared to DMSO control as studied by Western blot analysis.
2. Cefuroxime caused about 2 fold increase in the secretion of intracellular PAR-4 from the mouse embryonic fibroblast cells when compared to DMSO control as studied by Western blot analysis.
3. Albumin and collagen was used as a loading control for conditioned media.
4. Actin was used as loading control for lysate. 5. Also the conditioned media was cytotoxic to various panel of cancer cell lines.

Cefuroxime Axetil for Oral Suspension

| Ingredients | Qty. mg/g |
|---|---|
| Cefuroxime axetil | 20-500 |
| Polysorbate 80 | 0.25-0.50 |
| Simethicone | 0.6-1.0 |
| Xanthan gum | 10-20 |
| Silicon dioxide | 7.5-12.5 |
| Titanium dioxide | 15-20 |
| Sodium benzoate | 6-10 |
| Cherry flavor, natural and artificial (microencapsulated) | 2.5-5.0 |
| Sucrose | q.s.t. 1000 mg |

Cefuroxime axetil, xanthan gum, silicon dioxide, titanium dioxide, sodium benzoate, cherry flavor and a portion of sucrose were sifted. Polysorbate 80 and Simethicone were combined with a portion of sucrose and sifted. The two mixtures were then blended. The resulting blend was filled in white translucent HDPE bottle with cap and sealed using induction sealer.

Cefuroxime Axetil Suspension

| Ingredients | Quantity mg/mL |
|---|---|
| Cefuroxime axetil | 20-500 |
| Sorbitol solution 70% | 30-300 |
| Saccharin | 15-30 |
| Cherry flavor | 2.5-5 |
| Water purified | q.s.t. 1 mL |

Cefuroxime axetil was added to the sorbitol solution and mixed vigorously to form a suspension. Saccharin and cherry flavor were dissolved in purified water and added to the suspension. The desired volume was achieved by addition of purified water.

Cefuroxime Axetil Tablets

| Ingredients | Quantity mg/tablet |
|---|---|
| Cefuroxime axetil | 20-750 |
| Lactose monohydrate | 30-250 |
| Microcrystalline cellulose (Avicel PH 101) | 40-300 |
| Pregelatinized starch | 30-90 |
| Croscarmellose sodium | 15-45 |
| Poloxamer 188 (Pulmonic F 68) | 5-20 |
| Silicon dioxide colloidal | 2.5-10 |
| Magnesium stearate | 3-10 |
| Purified water | q.s |
| Coating | |
| Opadry ready mix | 10-25 |
| Purified water | qs |

Cefuroxime axetil, lactose monohydrate, microcrystalline cellulose, pregelatinized starch, and a portion (one-half) of croscarmellose sodium were sifted. The sifted powders were loaded in a suitable mixer/granulator and mixed. Poloxamer 188 was dissolved in a sufficient quantity of purified water, and the solution was used to wet granulate the mixed powder. Granules were dried and then blended with pre-sifted silicon dioxide, microcrystalline cellulose, and croscarmellose sodium. The blend was lubricated using pre-sifted magnesium stearate, compressed into tablets and coating with opadry ready mix.

Cefuroxime for Injection

| Ingredients | Qty/vial (mg) |
|---|---|
| Cefuroxime sodium | 20-750 |
| Dextrose hydrous, USP | 40-1500 |
| Sodium citrate hydrous | 250-500 |
| Hydrochloric acid for pH adjustment | q.s |
| Sodium hydroxide for pH adjustment | q.s |
| Water for injection, USP | Qst 2 mL |

Dextrose hydrous and sodium citrate hydrous were dissolved in freshly distilled water. Cefuroxime sodium was added and stirred to dissolve. The pH of the solution was adjusted to 5.0-7.5 using hydrochloric acid or sodium hydroxide and volume was made up with water. The solution of step 3 was filtered through a 0.22-μm filter and filled aseptically into vials and freeze dried.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for treating cancer, comprising increasing expression of prostate apoptosis response 4 in a patient having cancer by administering one or more anti-cancer agents consisting of cefuroxime, a pharmaceutically acceptable salt or prodrug thereof, in combination with an anti-cancer agent selected from the group consisting of ado-trastuzumab, ado-transtuzumab emtansine, alemtuzumab, atezolizumab, bevacizumab, blinatumomab, brentuximab vedotin, cetuximab, daratumumab, denosumab, dinutuximab, elotuzumab, gemtuzumab, gemtuzumab ozogamicin, ipilimumab, ibritumomab tiuxetan, necitumumab, nivolumab, obinutuzumab, ofatumumab, pantitumumab, pembrolizumab, pertuzumab, ramucirumab, rituximab, siltuximab, tositumomab, trastuzumab, vemurafenib, and combinations thereof.

2. The method according to claim 1, wherein the cefuroxime, a pharmaceutically acceptable salt or prodrug thereof, is administered in combination with a monoclonal antibody selected from ado-trastuzumab, and ado-trastuzumab emtansine.

3. The method according to claim 1, wherein the cefuroxime prodrug comprises cefuroxime axetil.

4. The method according to claim 1, further comprising administering ionizing radiation to the patient, performing a surgical intervention on the patient, or a combination thereof.

5. The method according to claim 4, wherein the cefuroxime is administered for a period of at least one week prior to commencing radiation treatment or surgical intervention.

6. The method according to claim 1, wherein the cefuroxime and additional anti-cancer agent are administered in an intermittent dosing regimen.

7. The method according to claim 1, wherein the cefuroxime and additional anti-cancer agent are administered simultaneously.

8. The method according to claim 1, wherein the cefuroxime and additional anti-cancer agent are administered separately.

\* \* \* \* \*